United States Patent [19]

McAllester

[11] 4,397,309
[45] Aug. 9, 1983

[54] PROTECTIVE STACK COVER FLAPS FOR FOLDED DRAPES

[75] Inventor: Spears L. McAllester, Bartlett, Tenn.

[73] Assignee: The Buckeye Cellulose Corporation, Cincinnati, Ohio

[21] Appl. No.: 236,477

[22] Filed: Feb. 20, 1981

[51] Int. Cl.³ .............................................. A61F 13/00
[52] U.S. Cl. .................................................. 128/132 D
[58] Field of Search ........................... 128/132 D, 292

[56] References Cited

U.S. PATENT DOCUMENTS

| 3,537,446 | 11/1970 | Rowland | 128/132 |
| 3,791,381 | 6/1974 | Krzewinski | 128/132 D |
| 3,910,268 | 10/1975 | Miller | 128/132 |
| 3,926,185 | 12/1975 | Krzewinski | 128/132 |
| 3,930,497 | 1/1976 | Krebs et al. | 128/132 |
| 4,119,093 | 10/1978 | Goodman | 128/132 |
| 4,354,486 | 10/1982 | Oliver | 128/132 D |

Primary Examiner—Michael H. Thaler
Attorney, Agent, or Firm—Milton B. Graff, IV; John V. Gorman; Richard C. Witte

[57] ABSTRACT

A folded surgical drape has protective flaps which protect against potential contamination of the sterile, operation-side surface of the drape. For a drape that is commonly folded in the lateral direction utilizing fan folds such that two juxtaposed stacks of panels are formed, an extra flap of material is retained at the top of each fan folded stack which is folded down along the side of each stack adjacent to the other stack and tucked between the lowermost pair of drape panels of the stack.

11 Claims, 10 Drawing Figures

U.S. Patent  Aug. 9, 1983  Sheet 2 of 4  4,397,309
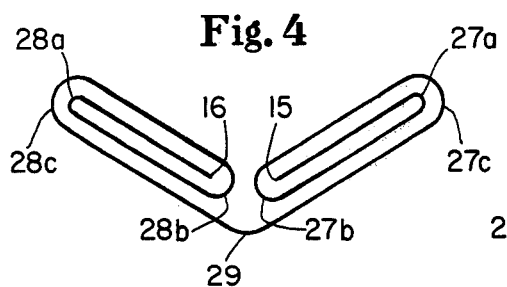
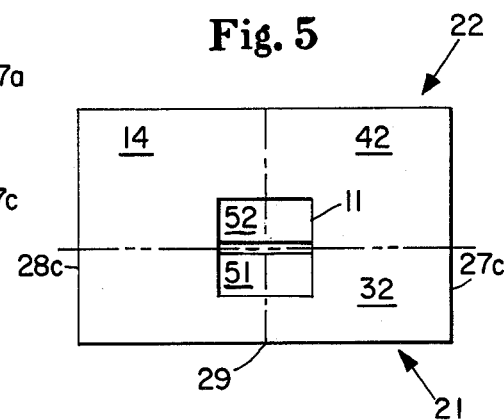
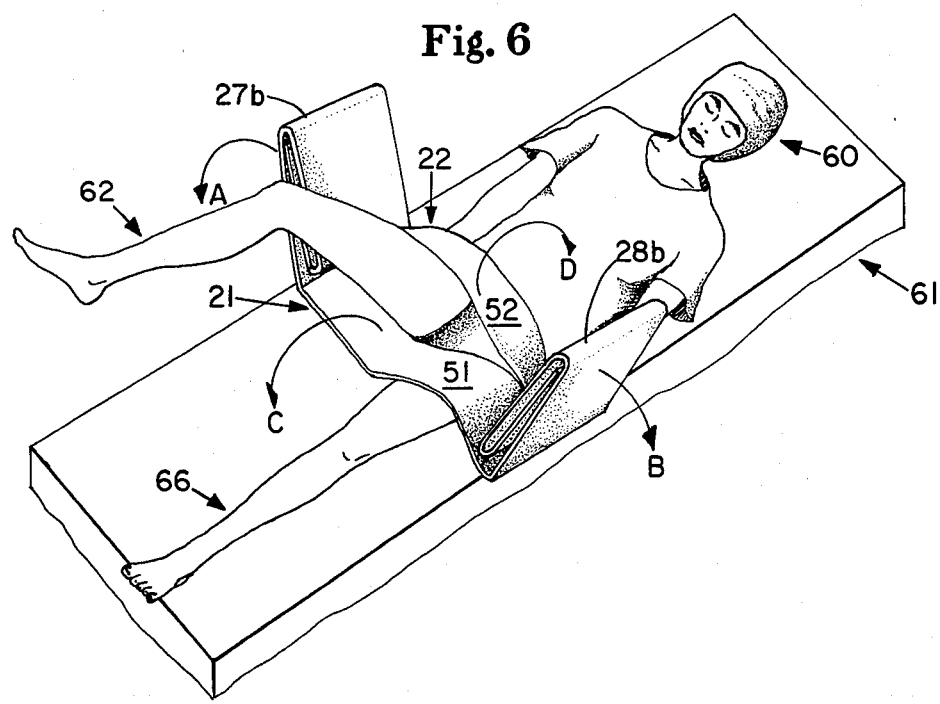

PROTECTIVE STACK COVER FLAPS FOR FOLDED DRAPES

TECHNICAL FIELD

This invention relates to a drape for use in a surgical operation and, more specifically, to a folding pattern for such a drape.

BACKGROUND ART

Disposable surgical drapes made of nonwoven fabrics are in common use. Such drapes are generally supplied by manufacturers in a prefolded, wrapped, sterilized condition. It is important that the drape be wrapped and folded in such a manner that it can easily be unwrapped and unfolded without contaminating the portions of the drape which are desired to remain sterile during the operation. For a drape to be used to cover a patient during a surgical operation, one of the primary purposes of using the drape is to separate the nonsterile patient from the sterile operating personnel and equipment. Therefore, the bottom surface or patient side of the drape is not expected to remain sterile during the operation while the top surface or operation side of the drape is generally expected to remain sterile.

A very popular folding technique used for surgical drapes is fan folding in which forward and reverse folds are alternated. This technique is popular because the entire portion of the drape fan folded can be unfolded simply by grasping the edge of the top panel and pulling it away from the folded drape. Thus the drape can be unfolded with a minimum amount of handling and a corresponding minimum chance of contamination.

For a drape to be used to cover a patient, it is generally desirable to set the folded drape on the patient and to unfold the drape toward all sides with a minimum amount of handling and shifting of the position of the drape. In order to accomplish this, the exposed under side of the folded drape is generally a part of the bottom surface or patient side of the drape which is near the center of the drape; commonly it is designed to be positioned over the operation site of the patient. The folded drape is placed on the patient in the proper position and is then unfolded to all sides, thus covering the patient. Such drapes are generally folded such that the exposed outer surfaces of the folded drape are largely portions of the bottom surface of the drape.

It is very common to have a fenestration, i.e. an opening, in a drape. Since the fenestration generally corresponds to the site where surgery will take place, the fenestration is commonly exposed on the outside of the folded drape so that it can be positioned properly prior to unfolding the drape. This can pose a potential problem since the drape surface exposed through the fenestration is generally a portion of the top surface of the drape which must be maintained sterile; this is particularly true for fan folded drapes. This potential problem is often solved by placing a piece of paper covering the fenestration on the top side of the drape prior to folding the drape. When the drape is folded, the paper is exposed through the fenestration rather than a portion of the top surface of the drape; the paper is removed after the drape is unfolded.

A fenestrated drape as described above is often used for surgery on an extremity. It is usually desired to have the extremity extend through the fenstration so that it rests on the top surface of the unfolded drape. Often the extremity is covered by a separate drape while the remainder of the patient is covered by the fenestrated drape. For ease of placing the drape, it is common to have an extremity drape folded into two oppositely disposed, juxtaposed stacks of folds with their lowermost panels contiguous and the fenestration within the lowermost panels, such that the extremity can be extended through the fenestration and between the folded juxtaposed stacks of the drape prior to unfolding. In this situation, a protective paper inside the folded drape cannot be readily used unless it can be removed prior to unfolding the drape. For common folding patterns, especially fan folding into the stacks described above, the act of extending the extremity through the fenestration and between the folded stacks of the drape causes the extremity to contact and contaminate portions of the top surface of the drape which are exposed on the adjacent sides of the stacks of folds.

Extremity drapes of special design have been used to avoid the potential contamination which occurs when using a simple fenestrated drape. U.S. Pat. Nos. 3,910,268 issued on Oct. 7, 1975, to Miller and 3,926,185 issued on Dec. 16, 1975, to Krzewinski disclose split sheet drapes designed for extremity surgery which have extra flaps so that they can be placed around the extremity and overlapped to isolate the extremity to be operated on from the rest of the patient. U.S. Pat. No. 3,930,497 issued on Jan. 6, 1976, to Krebs also utilizes a split sheet so that it can be placed around the extremity; Krebs uses adhesive tapes along the split so that it can be secured in position around the extremity. U.S. Pat. No. 4,119,093 issued Oct. 10, 1978, to Goodman discloses a collapsible sock which is attached to the fenestration and into which the extremity is inserted, thus the extremity does not touch and contaminate the top side of the drape as it is inserted through the fenestration and the folded drape.

DISCLOSURE OF THE INVENTION

The present invention concerns a surgical drape having a top surface and being folded to provide a stack of superposed drape panels. The stack comprises drape panels defined by a plurality of parallel folds such that portions of the top surface of the drape are exposed only along one side of the stack. A protective flap extends from an upper drape panel of the stack, around the one side of the stack, thus covering the exposed portions of the top surface of the drape, and is tucked beneath a lower drape panel of the stack.

BRIEF DESCRIPTION OF THE DRAWINGS

FIG. 4 is an enlarged cross-sectional view of the drape of FIGS. 1-3 as folded transversely with the edge of the laterally folded drape shown as a single line.

FIG. 5 is a bottom view of the folded drape of FIG. 4.

FIG. 6 is a fragmentary perspective view of the drape of FIGS. 1-5 after the insertion of a patient's leg through the fenestration but before unfolding of the drape.

It should be noted with respect to FIGS. 2, 4, 7, and 10 that the dimensions of the folds, stacks, etc., are exaggerated for clarity of the folded structure.

DETAILED DESCRIPTION OF THE INVENTION

Figure 1:
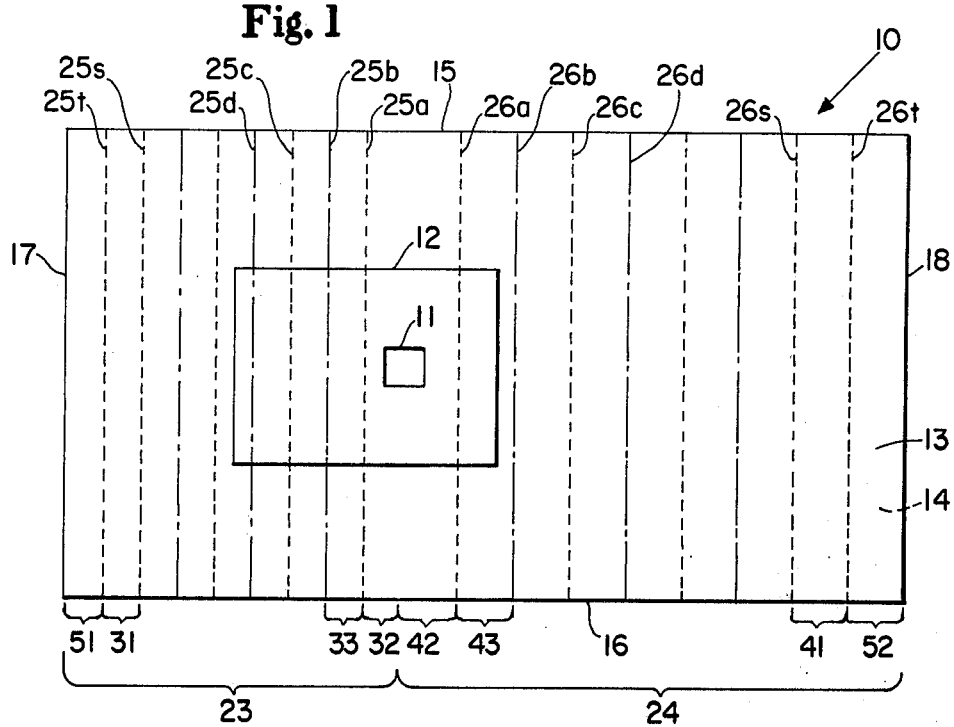
FIG. 1 is a plan view of the top surface of a preferred embodiment of a drape of the present invention, before folding.

Referring to the drawings wherein like reference characters are utilized to identify like parts through the several views, there is illustrated in FIG. 1 a fenestrated, reinforced, rectangular surgical drape 10. The drape 10, shown in FIG. 1 has a top surface 13 and a bottom surface 14, a pair of opposed longitudinal edges 15 and 16, and a pair of opposed lateral edges 17 and 18.

In a preferred embodiment, the drape 10 is made of a nonwoven fabric such as that described in U.S. Pat. No. 4,113,911 issued on Sept. 12, 1978, to LaFitte et al., the disclosure of which is hereby incorporated by reference. The drape has a fenestration or opening 11 and a reinforcing patch 12 around the fenestration; the reinforcement layer can be a fluid-impervious material adhesively attached to the top surface 13 of the drape. A preferred reinforcing material is a three-layer laminate, about 0.25 mm. in thickness, marketed by the 3M Company, St. Paul, Minn. The laminate is made by adhering a carded rayon staple fiber web to each side of a polyethylene film by means of a latex adhesive to which an antistatic agent has been added.

The drape of the present invention is especially adapted for use as an extremity drape. Although there is nothing critical about the dimensions, a typical size for an extremity drape is 320 cm. long and 218 cm. wide. The fenestration is 30 cm. square and is located midway between the longitudinal sides and 122 cm. from one lateral side. The reinforcement patch is 109 cm. long and 76 cm. wide and is located centrally between the longitudinal sides and starts 53 cm. from the lateral side closest to the fenestration. If desired, an apertured elastomeric insert (not shown in the drawings) 36 cm. square can be centered at the fenestration and adhesively bonded between the nonwoven fabric and the reinforcement patch around the edges of the fenestration. The aperture can be a circular hole 5.7 cm. in diameter through which the extremity is passed and which is designed to cause the insert to fit tightly around the extremity. A preferred elastomeric material is commercially available under the Trademark Kraton, a styrene-butadiene material, marketed by Shell Chemical Company, Houston, Tex.

Figure 3:
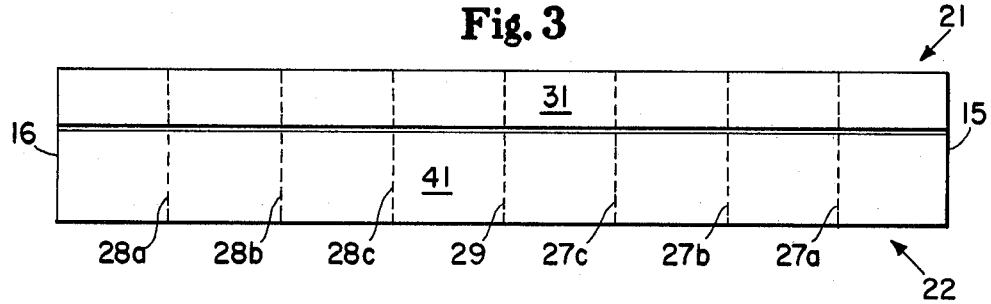
FIG. 3 is a plan view of the laterally folded drape of FIG. 2 before transverse folding.
Figure 9:
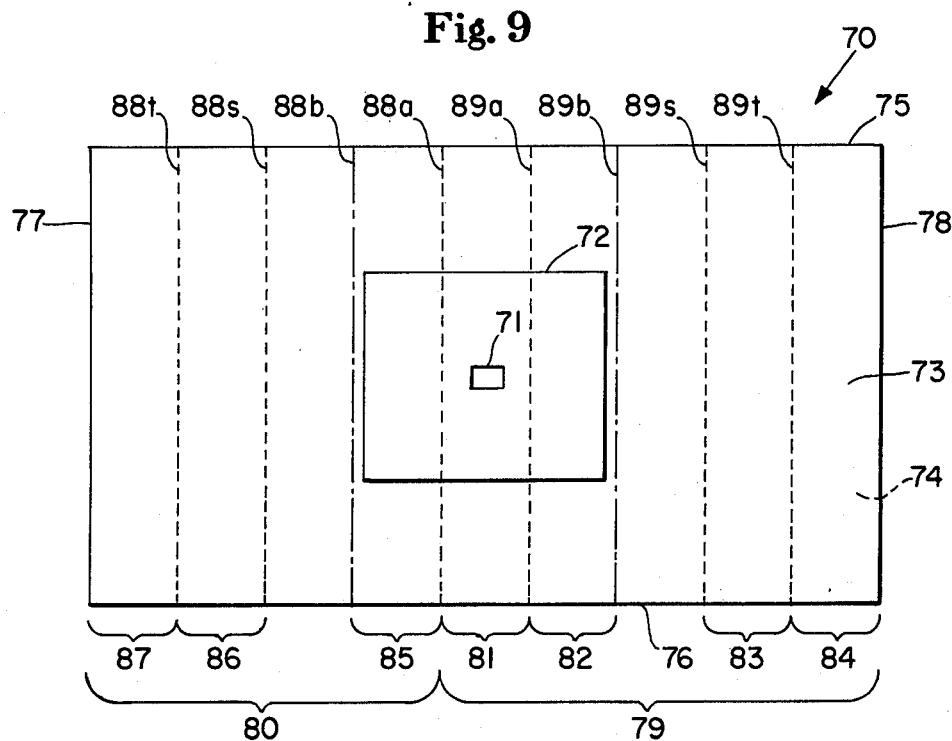
FIG. 9 is a plan view of the top surface of a second preferred embodiment of a drape of the present invention, before folding.

As used herein with reference to FIGS. 1 and 9, the term "forward fold" refers to a fold which brings portions of the top surface of the drape together while the term "reverse fold" as used herein is a fold which results in bringing portions of the bottom surface together. Similarly, with reference to FIG. 3, a "forward fold" refers to a fold which brings the upperside surfaces pictured therein together. The term "fan fold" as used herein refers to a folding pattern which is the result of alternating forward and reverse folds. In FIGS. 1, 3, and 9, a forward fold line is indicated by a dashed line made up of segments of equal length while a reverse fold line is indicated by a dashed line made up of alternating long and short segments.

Figure 2:
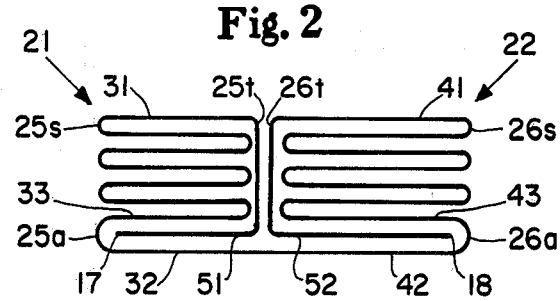
FIG. 2 is an enlarged cross-sectional view of the drape of FIG. 1 as folded laterally into stacks of folds.

Referring to FIG. 2, two juxtaposed stacks 21 and 22 of superposed laterally extending drape panels are formed by fan folding the opposed lateral edges 17 and 18 inwardly toward the center of the drape. Stack 21 is formed by fan folding lateral portion 23 of the drape, as shown in FIG. 1, beginning with a forward fold around fold line 25a and followed by alternate reverse and forward folds around parallel fold lines 25b, 25c, 25d, . . ., finishing with a forward fold around fold line 25s, to create a stack of panels of about equal size with a flap of material 51 left over. Stack 21 has an uppermost panel 31, a lowermost panel 32, and a second lowermost panel 33. The protective flap 51 of material extends from the uppermost panel 31 to the lateral edge 17 of the drape 10. Protective flap 51 is forward folded around fold line 25t down along the side of stack 21 which is adjacent stack 22 and is tucked between the lowermost panel 32 and the second lowermost panel 33. Stack 22 is constructed in a similar manner from lateral portion 24 of the drape by folding around fold lines 26a, . . ., 26t, thus creating uppermost panel 41, lowermost panel 42, second lowermost panel 43, and protective flap 52. The lowermost panels 32 and 42 of stacks 21 and 22 are contiguous.

The folding pattern shown in FIG. 2 results in a partially folded drape with only the bottom surface 14 of the drape being on any exposed portion. The upper sides of the uppermost panels 31 and 41, the lower sides of the lowermost panels 32 and 42, the exposed fold edges on the opposed sides of juxtaposed stacks 21 and 22, and the adjacent sides of protective flaps 51 and 52 are all parts of the bottom surface 14 of the drape. Thus FIG. 2 is an example of a surgical drape having a top surface which is folded to provide two oppositely disposed, juxtaposed stacks of superposed drape panels. Such a drape preferably has a fenestration which lies within contiguous lowermost drape panels of the stacks such as fenestration 11 lies within drape panels 32 and 42 of the drape shown in FIGS. 1 and 2. The stacks are each comprised of drape panels defined by a plurality of parallel folds, preferably fan folds as shown for the drape in FIG. 2. A protective flap extends from an upper drape panel, preferably from the uppermost drape panel, of each stack, around the side of the stack adjacent the other stack and between a lower pair of drape panels of the stack, preferably between the lowermost pair of drape panels of the stack. The protective flaps, such as flaps 51 and 52 depicted in FIG. 2, thereby cover a portion of the top surface of the drape on the edges of the folds which would otherwise have been exposed along the ajdacent sides of each stack.

The laterally folded drape, as shown in FIG. 3, is then transversely folded. A preferred mode of transversely folding the drape is shown in FIG. 4 with the laterally folded drape, composed of the stacks 21 and 22, shown as a single line in that figure. The laterally folded drape is transversely folded by a series of forward folds starting from the longitudinal edges 15 and 16 and progressing toward the center of the drape. Forward folds are made from longitudinal edge 15 around fold lines 27a, 27b, and 27c, and from longitudinal edge 16 around fold lines 28a, 28b, and 28c. A final book fold around fold line 29 results in a finished folded drape. FIG. 5 is a bottom view of the folded drape shown in FIG. 4 before making the book fold around the fold line 29; this book fold as viewed from the perspective of FIG. 5 is a reverse fold. The drape surfaces exposed through fenestration 11 are portions of the flaps 51 and 52. All exposed portions of the folded drape are a part of the bottom surface 14 of the drape.

To utilize the folded drape, the book fold around fold line 29 is opened so that the drape is as pictured in FIG. 5. Referring to FIG. 6, a patient 60 is reclined on an operating table 61 with the extremity 62 to be operated on held off the table. The extremity 62 is inserted through the folded drape starting from the surface shown in FIG. 5 through fenestration 11, between protective flaps 51 and 52, and between folds 27b and 28b. All portions of the drape contacted by the patient during this procedure are portions of the bottom surface 14 of the drape. The drape is then unfolded in the transverse direction as shown by the arrows A and B in FIG. 6 by reversing the transverse folds.

Figure 7:
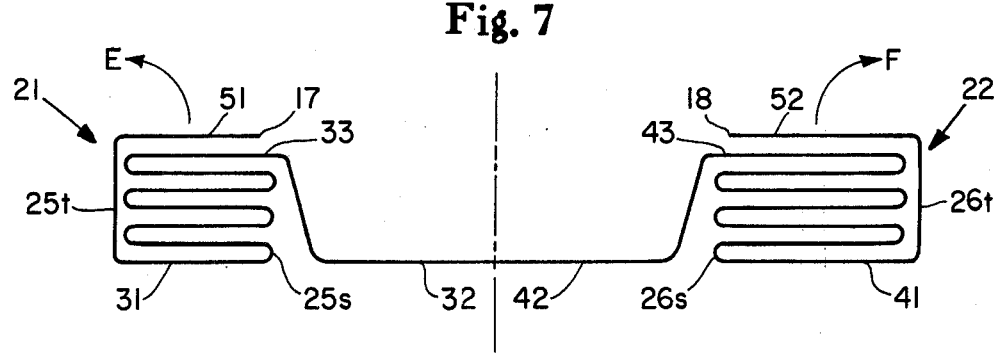
FIG. 7 is an enlarged cross-sectional view of the drape of FIGS. 1-6 after unfolding it transversely and illustrating its laterally folded condition after turning the stacks outwardly to expose the protective flaps of the present invention.
Figure 8:
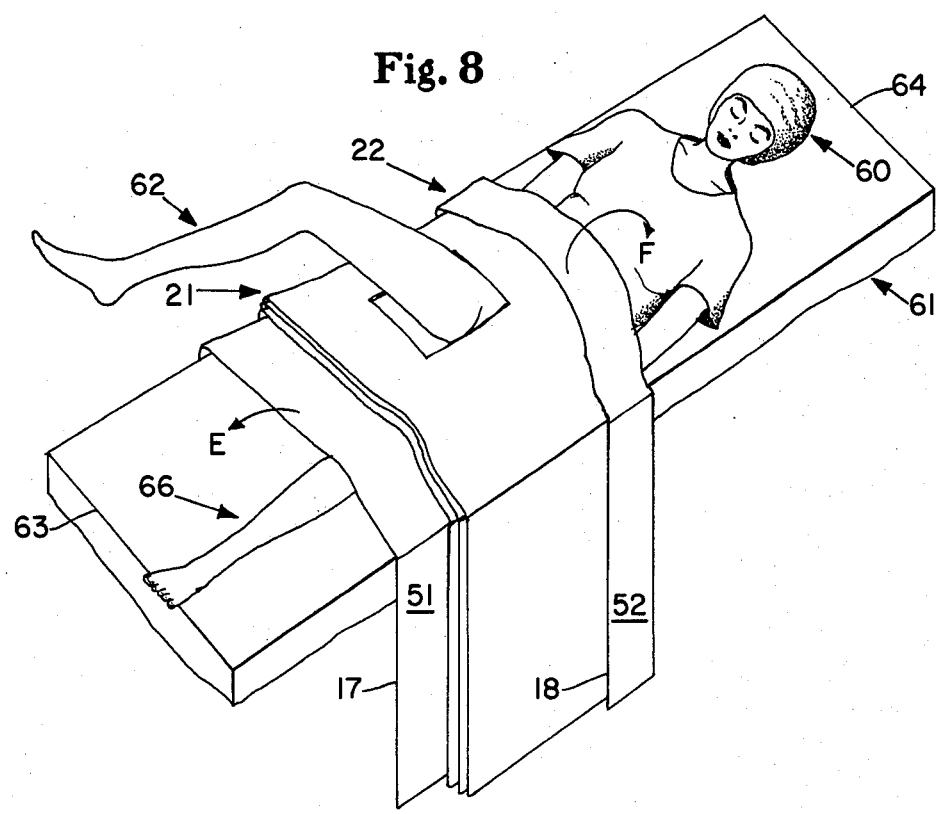
FIG. 8 is a fragmentary perspective view of the drape of FIGS. 1-7 positioned on a patient and being unfolded laterally.

The drape is unfolded in the lateral direction by first turning stacks 21 and 22 over as indicated by the arrows C and D in FIG. 6. The turning over of stacks 21 and 22 reverses the folds around fold lines 25a and 26a that are shown in FIG. 2. FIG. 7 shows a cross-sectional view of the laterally folded drape after stacks 21 and 22 have been turned over. By turning over stacks 21 and 22, protective flaps 51 and 52 are exposed. Lateral unfolding of the drape is completed by grasping flaps 51 and 52 and pulling them toward the opposed ends of the table as shown by Arrows E and F in FIGS. 7 and 8. Flap 51 is pulled in the direction indicated by Arrow E in FIG. 8 until the stack 21 is completely unfolded; lateral portion 23 of the drape is draped over the other leg and foot 66 of patient 60 and end 63 of table 61. Flap 52 is pulled in the direction indicated by arrow F in FIG. 8 until stack 22 is completely unfolded and lateral portion 24 of the drape is draped over the upper body of patient 60 toward end 64 of table 61. FIG. 8 pictures flap 51 as having been unfolded around fold line 25t and being ready to be pulled in direction E; flap 52 is still folded in the position as shown in FIG. 7.

Unfolding the drape in the manner described ensures that only the bottom surface 14 of the drape will contact the patient 60 and be contaminated. The top surface 13 of the drape remains sterile. After employing the draping procedure described herein, the extremity 62 to be operated on may be prepared for surgery in any of a number of ways. It is often wrapped or covered by a smaller drape made specifically for that purpose.

Figure 10:
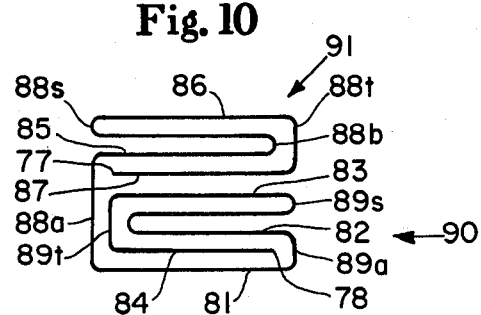
FIG. 10 is an enlarged cross-sectional view of the drape of FIG. 9 as folded laterally into stacks of folds.

Another embodiment of the present invention is illustrated in FIGS. 9 and 10 wherein the protective flap is used to eliminate the need for a protective paper over the fenestration. This embodiment could be utilized in fenestrated drapes having a wide variety of sizes.

There is illustrated in FIG. 9 a fenestrated, reinforced, rectangular surgical drape 70. Drape 70, shown in FIG. 9, has a top surface 73 and a bottom surface 74, a pair of opposed longitudinal edges 75 and 76, and a pair of opposed lateral edges 77 and 78. In a preferred embodiment, the drape 70 is made of the same materials of construction as described for the drape illustrated in FIG. 1.

A wide variety of fenestrated drapes of different sizes with different size and shape fenestrations could be depicted. A typical size for a fenstrated drape is 267 cm. long and 178 cm. wide. The fenestration is centered in the drape and is 13 cm. long and 5 cm. wide. The reinforcement patch is also centered in the drape and is 76 cm. long and 51 cm. wide. The forward and reverse folds used to fold the drape according to the present invention are illustrated in FIG. 9.

Referring to FIG. 10, two superposed stacks 90 and 91 of superposed laterally extending drape panels are formed by fan folding the opposed lateral edges 78 and 77 inwardly toward the center of the drape. Stack 90 is formed by fan folding the lateral portion 79 of the drape, as shown in FIG. 9, beginning with a forward fold around fold line 89a and following by alternate reverse and forward folds around parallel fold lines 89b, . . . , finishing with a forward fold around line 89s, to create a stack of panels of about equal size with a flap of material 84 left over. (The drape shown in FIGS. 9 and 10 has no folds between fold 89b and 89s, but a longer drape would have such folds.) Stacks 90 has an uppermost panel 83, a lower most panel 81, and a second lowermost panel 82. The fenestration 71 lies within the lowermost panel 81. The protective flap 84 of material extends from the uppermost panel 83 to the lateral edge 78 of the drape 70. The protective flap 84 is forward folded around fold line 89t and is tucked between the lowermost panel 81 and the second lowermost panel 82. Thus instead of a portion of the top surface of the drape (a part of second lowermost panel 82) being exposed through the fenestration 71, a portion of the bottom surface 74 of the drape, a portion of the protective flap 84, is now exposed through the fenestration. This eliminates the need for a fenestration protective paper which would normally be placed over the fenestration prior to folding the drape.

The portion of drape 70 which forms stack 90 as depicted in FIG. 10 provides an example of a surgical drape having a top surface and a fenestration which is folded to provide a stack of at least four superposed drape panels. The stack comprises drape panels defined by a plurality of parallel folds. A portion of the top surface of the drape which would otherwise be exposed through the fenestration is covered by a protective flap adjacent one edge of the drape which extends from a panel above the lowermost drape panel and between the lowermost pair of drape panels of the stack.

Stack 91 is constructed atop stack 90 by fan folding lateral portion 80 of drape 70 starting with a foward fold around fold line 88a and followed by alternate reverse and foward folds around parallel fold lines 88b, . . . . In a preferred embodiment, a protective flap can be used to cover the exposed portions of the top surface 73 of the drape along the side of stack 91 as illustrated by fold 88b in FIG. 10. This is accomplished by finishing the fan folding of stack 91 with a forward fold around fold line 88s thus creating stack 91 with uppermost panel 86 and lowermost panel 85 and a flap of material 87 left over. The protective flap 87 of material extends from the uppermost panel 86 down along the side of stack 91 thus covering the exposed upper surface of fold 88b, and is tucked between lowermost panel 85 and uppermost panel 83 of stack 90.

The folding pattern shown in FIG. 10 results in a partially folded drape with only the bottom surface 74 of the drape being on any exposed portion. The folded surgical drape depicted in FIGS. 9 and 10 is an example of a surgical drape having a top surface which is folded to provide a stack of superposed drape panels. The stack comprises drape panels defined by a plurality of parallel folds, preferably fan folds. A protective flap, comprising an edge of the drape, extends from an upper drape panel of the stack, preferably from the uppermost drape panel of the stack, around a part of one side of the stack which is below said upper drape panel and beneath a lower drape panel of the stack, preferably between the lowermost pair of drape panels of the stack. The protective flap thereby covers a portion of the top surface of the drape which would otherwise have been exposed along said part of the side of the stack. The laterally folded drape can then be transversely folded in the same manner as described for the drape shown in FIGS. 3 and 4.

While particular embodiments of the present invention have been illustrated and described, it will be obvious to those skilled in the art that various changes and modifications can be made without departing from the spirit and scope of the invention. It is intended to cover, in the appended claims, all such modifications that are within the scope of this invention.

What is claimed is:

1. A surgical drape having a top surface and being folded to provide a stack of superposed drape panels, said stack comprising drape panels defined by a plurality of parallel folds, and a protective flap, comprising an edge of the drape, which extends from an upper drape panel of the stack around a part of one side of the stack which is below said upper drape panel and beneath a lower drape panel of the stack, whereby a portion of said top surface which would otherwise have been exposed along said part of the side of the stack is covered by said protective flap.

2. The surgical drape of claim 1 wherein said drape has a fenestration, at least a portion of said fenestration lying within the lowermost drape panel, said lower drape panel being the second lowermost panel of the stack, whereby a portion of said top surface which would otherwise have been exposed through said fenestration is covered by said protective flap.

3. The surgical drape of claim 2 wherein said stack is fan folded and said upper drape panel is the uppermost drape panel.

4. The surgical drape of claim 1 wherein said stack is fan folded and said upper drape panel is the uppermost drape panel.

5. A surgical drape having a fenestration and being folded to provide a stack of superposed drape panels, said fenestration being in the lowermost drape panel, said stack comprising drape panels defined by a plurality of fan folds and a protective flap which extends from the uppermost drape panel of the stack, around one side of the stack and between the lowermost pair of drape panels of the stack.

6. A surgical drape having a top surface and being folded to provide two oppositely disposed, juxtaposed stacks of superposed drape panels, said stacks each comprising drape panels defined by a plurality of parallel folds and a protective flap which extends from an upper drape panel of the stack, around the side of the stack adjacent the other stack and between a lower pair of drape panels of the stack, whereby a portion of said top surface which would otherwise have been exposed along said side of the stack is covered by said protective flap.

7. The surgical drape of claim 6 wherein said drape has a fenestration, at least a portion of said fenestration lying within the lowermost panel of each of said stacks, said lower pair of drape panels being the lowermost pair of drape panels of each stack, whereby a portion of said top surface which would otherwise have been exposed through said fenestration is covered by said protective flaps.

8. The surgical drape of claim 7 wherein said stacks are fan folded, and said upper drape panel is the uppermost drape panel of each stack.

9. The surgical drape of claim 6 wherein said stacks are fan folded, and said upper drape panel is the uppermost drape panel of each stack.

10. A surgical drape having a fenestration therethrough and being folded to provide two oppositely disposed, juxtaposed stacks of superposed drape panels, said fenestration lying within contiguous lowermost drape panels of the stacks, said stacks each comprising drape panels defined by a plurality of fan folds and a protective flap which extends from the uppermost drape panel of the stack, around the side of the stack adjacent the opposed stack and between the lowermost pair of drape panels of the stack.

11. A surgical drape having a top surface and a fenestration and being folded to provide a stack of at least four superposed drape panels, said stack comprising drape panels defined by a plurality of parallel folds, and a protective flap adjacent one edge of said drape which extends from a panel above the lowermost drape panel and between the lowermost pair of drape panels of the stack, whereby a portion of said top surface which would otherwise have been exposed through said fenestration is covered by said protective flap.

* * * * *